United States Patent [19]

Giebeler

[11] Patent Number: 4,921,350

[45] Date of Patent: May 1, 1990

[54] MONOCHROMATOR SECOND ORDER SUBTRACTION METHOD

[75] Inventor: Robert Giebeler, Cupertino, Calif.

[73] Assignee: Beckman Instruments, Inc., Fullerton, Calif.

[21] Appl. No.: 309,502

[22] Filed: Feb. 10, 1989

[51] Int. Cl.⁵ ............................................. G01J 3/42
[52] U.S. Cl. .................................... 356/320; 356/328
[58] Field of Search ............... 356/319, 328, 332, 334, 356/300, 320

[56] References Cited

U.S. PATENT DOCUMENTS

| | | | |
|---|---|---|---|
| 3,628,849 | 12/1971 | Flamand et al. | 350/162 |
| 3,652,860 | 3/1972 | Walker | 250/218 |
| 3,712,742 | 1/1973 | Cohen | 356/197 |
| 3,721,487 | 3/1973 | Pieuchard et al. | 350/7 |
| 3,807,874 | 4/1974 | Gropper | 356/198 |
| 3,909,134 | 9/1975 | Piechard et al. | 356/99 |
| 3,930,728 | 1/1976 | Pieuchard et al. | 356/99 |
| 3,942,048 | 3/1976 | Laude et al. | 310/8.1 |
| 3,973,850 | 8/1976 | Pouey | 356/100 |
| 4,830,493 | 5/1989 | Giebeler | 356/328 |

FOREIGN PATENT DOCUMENTS 647598 1/1985 Switzerland .

Primary Examiner—F. L. Evans
Attorney, Agent, or Firm—William H. May; Paul R. Harder

[57] ABSTRACT

In an optical system for measuring sample absorption of light at a primary wavelength output from a monochromator, a method of subtracting the effect of secondary wavelength components of light from the monochromator. The sample absorption of light at the primary wavelength including the effect of the secondary wavelength components and at the secondary wavelength are determined. The results are used to obtain the sample absorption of light at the primary wavelength without the effect of the secondary wavelength components.

4 Claims, 2 Drawing Sheets

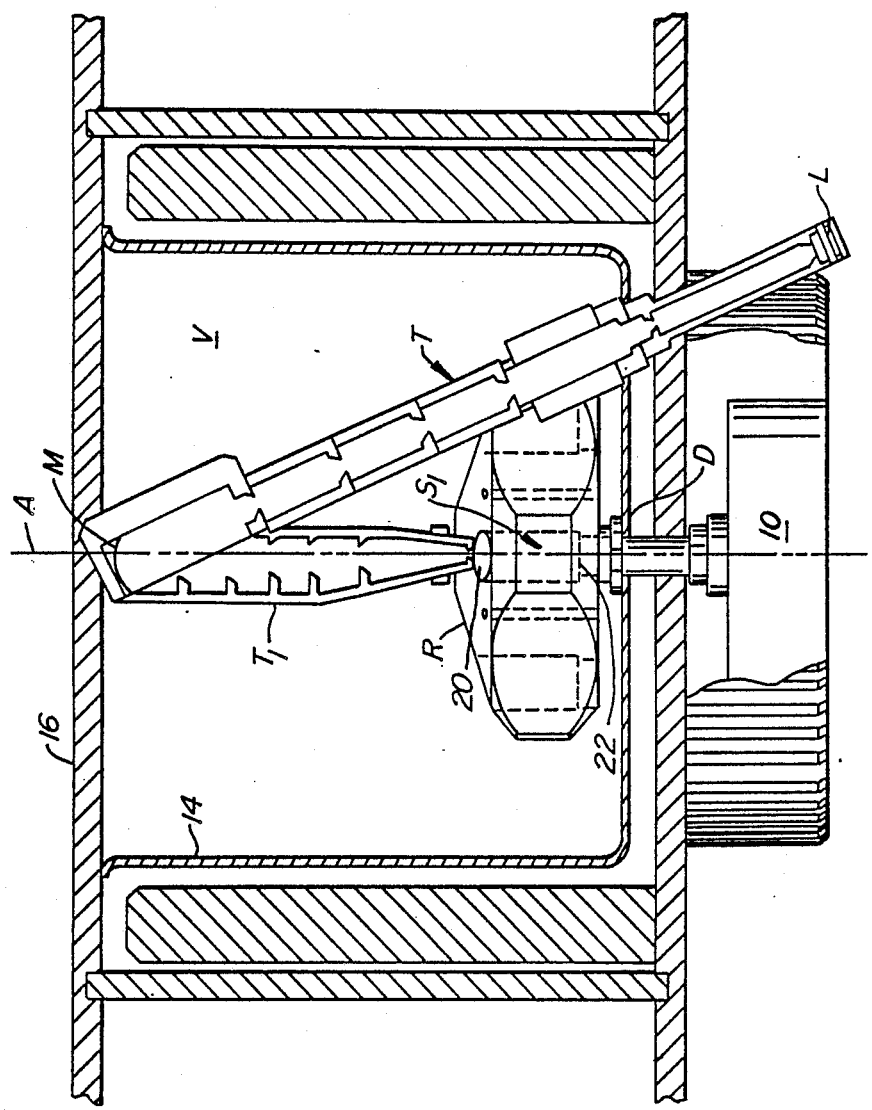

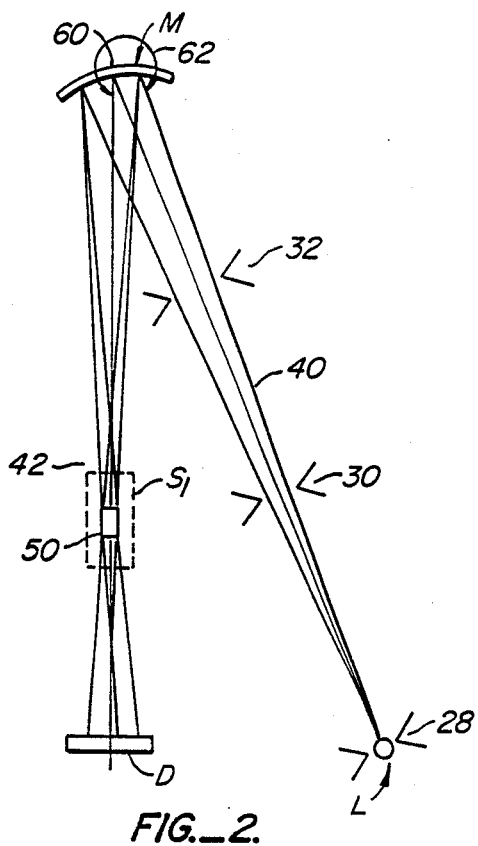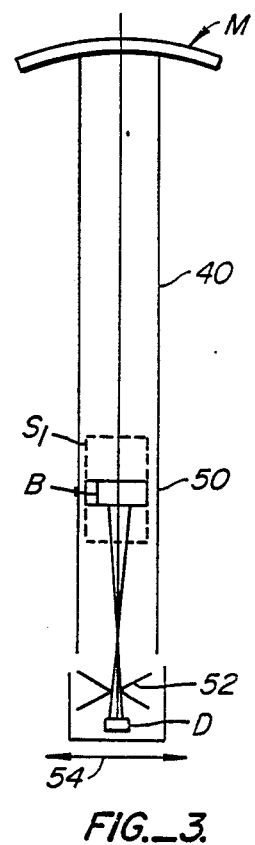
FIG._2.   FIG._3.

MONOCHROMATOR SECOND ORDER SUBTRACTION METHOD

BACKGROUND OF THE INVENTION

This invention relates to the interrogation of samples by monochromatic light and, in particular, relates to a diffraction grating produced monochromatic light and an apparatus and process for screening out half order wavelength effects from diffraction gratings.

1. Statement of the Problem

It is common to observe during centrifugation separation of sample. Typically, a centrifuge rotor is provided. The rotor includes a so-called sample cell and a reference cell. To enable the observation, the sample cell and the reference cell are supplied with windows. Light is transmitted through both sample cell and the reference cell.

The reference cell and the sample cell preferably both contain a solvent having a gradient forming solute therein. During the centrifugation process, the absorption of the light radially across the reference cell provides an indication of solvent and solute gradient in both the reference cell and the sample cell. The relative absorption of light radially across both sample cell and the reference cell provide an indication of sample separation. By observation of both the solute gradient in the solvent and sample separation, analysis may be made and distribution in the gradient forming solute within the solvent.

For such light of the sample/absorption measurement, monochromatic light has been used. Typically, measurements are taken in a variety of discrete wavelengths. By observation of light absorption of a sample cell versus a reference cell at the same discrete wavelength, identification, quatification, and related analysis of the components of the sample can be made.

It has been known to utilize narrow band pass filters to produce the desired monochromatic light. Unfortunately, these filters are large, have many optical interfaces and are expensive. Further, where several wavelengths are utilized, the mechanical problem of sorting, inserting and removing the filters to and from the interrogating light path complicates filter usage.

2. Related Art

In a related disclosure entitled UV Scanning System for Centrifuge. Ser. No. 07/115.023, filed Oct. 29. 1987, now U.S. Pat. No. 4,830,493, I have disclosed the use of a diffraction grating for producing monochromatic light for sample absorption analysis. Simply stated. I disclose a mirror diffraction rule parallel to a tilting axis to produce monochromatic light. The mirror has a figure along the length of the axis with appropriate curvature to produce collimated interrogating light. By the expedient of tilting the mirror, interrogation of windowed cells in a rotating rotor can occur by monochromatic collimated light beams during the process of centrifugation.

DISCOVERY OF THE PROBLEM

In the use of the diffraction grating classified light for the light absorption analysis of samples in solvents and solutes, relatively great attenuation of the monochromatic light beam can occur, often to more than one order of magnitude. Inevitably present in such diffraction grating classified light are second order light effects. These second order light effects have a component in the order of a magnitude less than the primary interrogating monochromatic beam. Frequently the primary monochromatic beam when attenuated by the optical density of the sample reaches the intensity of the half order chromatic component. This being the case, system measurement has been degraded. Accordingly, and once this problem was discovered, it was necessary to create an apparatus and process for the elimination of this effect.

Insofar as the problem herein discovered has not been addressed in the applicable prior art, invention is claimed.

SUMMARY OF THE INVENTION

In an instrument wherein a sample in a solvent with a solute is interrogated for absorption by monochromatic light, a method and apparatus for electronically measuring and subtracting the effect of half order chromatic components is disclosed. The light is originally produced by a relatively broad spectrum light source having its spectral output separated to a monochromatic interrogating beam produced by reflection at an angle from a diffraction grating. Inevitably present in such diffraction grating produced chromatic light are half order light components. The process includes turning the diffraction grating with respect to the light source to have a primary output in the frequency of the half order component of the selected primary monochromatic frequency and taking a measure of the system absorption at the half order component. System absorption can be taken either by passage through the system free of solvent, solute and sample or alternatively passage through a reference cell containing solvent and solute within the system. The diffraction grating is then turned with respect to the light source to have a primary output in the primary monochromatic frequency. The ratio of primary monochromatic frequency to half order transmission (a known constant for any diffraction grating) is utilized to calculate the half order component in any selected primary monochromatic frequency. Thereafter, and for a sample in a solvent and solute, the log of the ratio of absorption of all light less the calculated half order light absorption for the sample in the solute and the solvent over the absorption of all light for the system less the calculated half order light absorption for the system is taken to describe relative light absorption. It is preferred to use a reference cell for the system absorption measurement to describe relative light absorption between the sample cell and reference cell. Utility can be present in comparing the absorption between differing solvents, solutes or samples. The apparatus and method finds preferred utility in observing centrifugation induced separation through windows in a spinning rotor during the process of separation.

OTHER OBJECTS, FEATURES AND ADVANTAGES

An object to this invention is to set forth an apparatus and process for use with a diffraction grating classified light to eliminate the effects of half order components from monochromatic light absorption analysis. Accordingly, the system absorption is first measured at the half order wavelength involved by tilting the diffraction grating to have a primary output at the half order wavelength. System absorption at the half order wavelength is measured. Once this is done, the contribution of the half order wavelength at the primary wavelength is calculated, this calculation occurring as a known constant of the primary wavelength output of the diffraction grating. The calculated half order contribution is then subtracted from the total observed light to determine the correct reading of light intensity at the chosen primary chromatic frequency.

An advantage of this disclosed apparatus and process is that primary utility is found for observing through windowed cells in a centrifuge rotor the dynamics of centrifugal separation. The preferred use of the system includes checking system absorption through a reference cell in the centrifuge rotor having solvent and solute and comparing the resultant absorption to a sample cell having the same solvent, solute and an injected sample for separation. The system also finds utility in comparing different concentrations of solvents and solutes, or for observing a single classification without a reference sample (presuming overall system absorptions are known).

A further advantage of the disclosed apparatus and process is that the insertion and removal of numerous filters are not required.

Yet another advantage of the disclosed apparatus and process is that the disclosed second order subtraction technique can be carried out for each and every measurement occurring during the duration of a separation. This being the case, changes in the system do not effect the measurement taken. For example, where a light source ages and changes in spectral output, the use of the process and apparatus of this invention effectively updates instrument measurement to be independent of such spectral changes.

An additional advantage of this invention is that the subtraction technique imparts flexibility to the choice of the particular monochromatic light utilized for sample interrogation. Simply stated, the diffraction grating can be varied to produce light at any number of primary frequencies. Dependent upon the particular primary frequency chosen measurement and subtraction can occur of the half order of that particular chosen frequency. Within the limits of the chromatic output of the rulings on the diffraction grating many discrete interrogating frequencies can be chosen and their half order components determined and thereafter subtracted. This same variation of light frequency cannot be present where discrete filters having fixed narrow band pass wavelengths are utilized.

Another advantage of this invention is that the source can be chosen to be limiting in its output wavelength to simplify the problem of subtracting the second order effects. By the expedient of choosing a source that outputs the primary wavelength and the first half order wavelength, but omits the second and all shorter half order wavelengths, the subtraction of lesser order wavelengths is obviated. Indeed, the preferred embodiment of this invention includes a primary interrogating frequency in the order of 400 nanometers, and a secondary emission from the diffraction grating in the order of 200 nanometers. A broad band light source is chosen but does not emit in the range of 100 nanometers. Thus the only undesired emission from the diffraction grating is in the 200 nanometer wavelength.

Other objects, features and advantages of this invention will become more apparent after referring to the following specification and attached drawings in which;

FIG. 1 is a side elevation section of a centrifuge having a light interrogating system utilizing a mirror ruled for diffraction of light parallel to a tilt axis and figured along the tilt axis for collimated of the output monochromatic rays;

FIG. 2 is a radial side elevation of the light source path taken along the spin axis of the centrifuge in FIG. 1; and FIG. 3 is a side elevation section taken normal to the elevation of FIG. 2.

Referring to FIG. 1 a so-called "ultracentrifuge" is illustrated. Simply stated, a motor 10 spins a rotor R about an axis A. High speeds are involved. It is not uncommon for rotor R to spin at 100,000 revolutions per minute. As is well known in the art. centrifuging occurs in a vacuum to avoid windage. A sample is contained within a cell S1. The cell includes an upper window 20 and a lower window 22 permitting light to pass parallel to the spin axis of the rotor R. It is through these respective windows that a light beam formed in accordance with the teaching of this invention performs the method of examining sample stratification and reference cell density while centrifuging dynamically occurs.

Regarding the light, a tube T has a light L transmitted to impinge on a mirror M. Light from mirror M is reflected down through a folded tube T1 and passes through windows 20. 22 in cell S1 of rotor R. After passing through the respective windows 20. 22 light is incident upon a detector D. See FIGS. 2 and 3. As will hereinafter be illustrated, detector D is a moving slit capable of having an excursion over the radial length of the sample and reference cells.

Forces produced by the centrifuge typically range between five thousand (5,000) gravity fields to a half-a-million (500,000) gravitational fields. It is the purpose of this invention to intimately examine strata dynamically forming as the process of centrifugation continues. It will be appreciated the cessation of centrifuging to observe the sample may well destroy the very result that the centrifugation is attempting to create. Specifically, stratification that can occur under large gravitational fields produced often dissipates by way of diffusion once the large gravity fields are removed.

In the following application, it is necessary to define certain planes. These planes, once defined, will allow the configuration of the particular diffraction optics illustrated in FIGS. 2 and 3 to be discussed.

First, the sample is typically disposed at a sample point where the sample is optically read for stratification. The sample point lies along a radius from the spin axis A of the centrifuge. Observing FIG. 3, the view of the optics there shown is taken normal to a radius extending from the spin axis to the sample.

It is also necessary to describe a plane at right angles to the sample plane. This plane is the dispersion plane and is the plane along which chromatic dispersion or separation of the light occurs from the diffraction grating rule mirror M. This dispersion plane is the plane of FIG. 2.

Having set these respective planes, the function of the preferred specialized optics of this invention can be set forth. This function includes collimation of the light in the plane of FIG. 3 to produce a collimated interrogation of the sample by monochromatic light.

Referring to FIG. 2 a strobe light L passes through an aperture 28 preferably 1 millimeter or less in diameter. Light 40 from the light source passes through the respective tube stops 30 and 32 and is incident upon a mirror M.

Referring to FIG. 3 the reader will understand that light source L is not shown. FIG. 3, however, does show light 40 emanating downwardly from mirror M through sample 50 past a slit detector 52 to and upon a detector D. It will be understood that slit 52 scans underneath the sample 50. In such scanning it will identify strata precisely parallel to the spin axis A and normal to the sample plane of FIG. 3.

Mirror M is here given a cylindrical shape with respect to the light source L in the sample plane of FIG. 3. This cylindrical shape is chosen so that the rays 40 are precisely collimated with the plane of FIG. 3 along a path parallel to the spin axis of the rotor R. Thus classified layers of sediment such as that existing at band B have the collimated rays 40 precisely parallel to and through the band B.

Mirror M is shaped along one axis for the generation of collimated rays. Along the other axis the mirror is provided with different curvature and differently spaced ruling so that tilting of the mirror produce lights of varying color.

Such rulings are known. See Pieuchard et al. U.S. Pat. No. 3,909,134 issued Sept. 30, 1975. Additional relevant prior art relating to the construction of such mirrors may be found in Pieuchard et al. U.S. Pat. No. 3,930,728 issued Jan. 6, 1976; Pieuchard et al. U.S. Pat. No. 3,721,487 issued Mar. 20, 1973; Laude et al. U.S. Pat. No. 3,942,048 issued Mar. 2, 1976; and Flamand U.S. Pat. No. 3,628,849 issued Dec. 21. 1971.

Rotation of grating to change wavelength occurs about 30° from normal to the light source. Effective curvature for collimation does not change regardless of grating angle.

The reader will understand that the illustrated optics are preferred. Other optics that collimate the light in the sample plane only can be used. For example combinations of lenses and mirrors could be used.

It will be understood that slit 52 traverses the detector D back and forth along the path indicated by double arrow 54. In such a traverse, detector D will see the differences in the receipt of light as described in Cohen U.S. Pat. No. 3,712,742 issued Jan. 23. 1973.

Some numerical examples can be useful. Specifically light source L is typically a strobed xenon source. At the instant of strobing the light source includes output in the range of 20,000 watts.

Great attenuation of the light can occur through the essentially opaque layers such as band B in sample 50 inside cell S1. Light attenuation on the order of 17 decades ($10^{17}$) overall can occur. Light attenuation at the sample can be 3 decades ($10^3$).

Referring back to the view of FIG. 2, it is also desirable to scan the sample 50 in cell S1 with chromatically classified bands. For example, it is desired to scan proteins being classified in centrifuges in the range of 200 to 800 nanometers or higher (this range being in the ultraviolet and visible portion of the optical spectra). Accordingly, mirror M is provided with curvatures having unequal spaced rulings in the plane of FIG. 3. As viewed in FIG. 2, the rulings extend into and out of the plane of the drawing. By the expedient of turning the mirror about an axis 60 as illustrated by arrow 62, scanning of sample 50 can occur in 5 nanometer wide bands. The reader will understand that the width of the scanning optical bands or band pass is in effect determined by the solid angle of mirror radiation defined through windows 20. 22 as viewed in FIGS. 2 and 3.

It will be understood that measurements will be taken for any individual centrifugation over a period of several hours (or even days). Accordingly, and before each measurement at a selected wavelength lambda ($\lambda$), measurement of the system absorption will first occur at the respective half order wavelength. Thereafter, and for the particular primary wavelength selected, a so-called first order/second order factor $C_o$ will either be input or preferably obtained from a look-up table.

Thereafter, system sensitivity ($S\lambda$) i.e. including the combined effect of the tube emission, grating transmission and detector sensitivity of the optical system, at the primary wavelength is calculated by taking the total light received ($S\lambda^*$) and substracting out the system sensitivity ($S\lambda_{/2}^*$). This calculation will be made by the following formulae:

$$S_\lambda = S_\lambda^* - C_o \times S_{\lambda/2}^* \; (S_{\lambda/2} = S_{\lambda/2}^*)$$

In this calculation, it is assumed that only the second order wavelength is present to degrade the first order emission. This assumption is accurately made for in the example here given, emission of the light source at lower orders does not occur. By way of example, and assuming interrogation in the range of 400 nanometers, 200 nanometers will be the lower order wavelength. The next lowest order will be 100 nanometers. Fortunately, the light source of the preferred embodiment does not emit at this wavelength.

The reader will understand that should lower orders occur, extrapolation of the equations herein set forth could approximate elimination of lower order components.

Once this calculation is made, the following factors are known:

$I_{\lambda/2}$—transmitted intensity through the system at the second order wavelength.
$S_{\lambda/2}$—sensitivity of the system at $\lambda/2$.
$S\lambda$—sensitivity of the system at the primary wavelength alone.
$C_o$—First order/second order factor.
$C_2$—Calibration factor (a experimentally determined system constant.)

From these known factors, the intensity of the second order light can be calculated ($I_{o\lambda/2}$) as follows:

$$I^o{}_{\lambda/2} = I_{\lambda/2} \times \frac{S_{\lambda/2}}{S_\lambda} \times C_{o\lambda} \times C_{c\lambda} \; (I_{\lambda/2} = I^*{}_{\lambda/2})$$

In a typical system light source illuminates diffraction grating and wavelength of interest passes through slit, then through reference or sample and then to detector.

If absorption measurement is to be made at $\lambda$ and there is light emission and detector sensitivity at $\lambda/2$, then $\lambda/2$ (second order) light will also pass through diffraction grating.

$$OD_\lambda = \log \frac{I_{S\lambda}}{I_{R\lambda}}$$

where I=Transmitted Intensity where only one order wavelength is present.
S=sample
R=reference
$\lambda$=wavelength
Absorption can be calculated when both $\lambda$ and $\lambda/2$ light is present:

$$OD\lambda = \log \frac{I^*_{s\lambda} - I^*_{s\lambda/2}}{I^*_{R\lambda} - I^*_{R\lambda/2}}$$

It can therefore be seen that, from the calculation, that determining the absorption at the primary wavelength is possible.

I claim:

1. In an optical system for measuring light absorption of a sample which comprises a monochromator which can selectively output a beam of light having a desired primary component at a first wavelength and an undesired secondary component at a second wavelength; a detector positioned to detect light output from the monochromator through the sample; and a sample cell for holding the sample in the light beam between the monochromator and the detector; a method of subtracting the effect of the secondary component of light from the measurement of the sample absorption at the primary component comprising the steps of:

(a) determining the system sensitivity to light at the second wavelength;
   (b) determining the system sensitivity to light at the first wavelength including the effect of the secondary wavelength component of light;
   (c) determining the system sensitivity to light at the first wavelength alone using the results of steps (a) and (b);
   (d) determining the sample absorption of light at the second wavelength by using the results of steps (a) and (c);
   (e) determining the sample absorption of light at the first wavelength including the effect of the secondary component of light; and
   (f) determining the sample absorption of light at the first wavelength alone by using the results of steps (d) and (e).

2. A method as in claim 1 wherein the monochromator in the optical system comprises a diffraction grating.

3. A method as in claim 2 wherein the second wavelength is the first half order of the first wavelength.

4. A method as in claim 1 wherein the sample cell includes first and second compartments, the first compartment contains a reference material and the second compartment contains the sample and wherein step (f) comprises the steps of determining the absorption of light by the reference material at the second wavelength and absorption of light by the reference material at the first wavelength including the effect of secondary component of light; and using the difference between said two reference absorptions and the difference between the sample absorptions of steps (d) and (e) to determine the sample absorption of light at the first wavelength alone.

* * * * *